(12) United States Patent
Wei et al.

(10) Patent No.: US 11,541,007 B2
(45) Date of Patent: Jan. 3, 2023

(54) PHARMACEUTICAL COMPOSITIONS CONTAINING MIXED POLYMERIC MICELLES

(71) Applicant: MegaPro Biomedical Co., Ltd., Zhubei (TW)

(72) Inventors: Ming-Cheng Wei, Taoyuan (TW); Yuan-Hung Hsu, Hsinchu (TW); Wen-Yuan Hsieh, Hsinchu (TW); Chia-Wen Huang, Hsinchu (TW); Chih-Lung Chen, Taichung (TW); Jhih-Yun Jian, Yilan County (TW); Shian-Jy Wang, Hsinchu (TW)

(73) Assignee: MegaPro Biomedical Co., Ltd., Zhubei (TW)

(*) Notice: Subject to any disclaimer, the term of this patent is extended or adjusted under 35 U.S.C. 154(b) by 0 days.

(21) Appl. No.: 16/414,193

(22) Filed: May 16, 2019

(65) Prior Publication Data
US 2020/0360287 A1  Nov. 19, 2020

(51) Int. Cl.
| | |
|---|---|
| *A61K 9/107* | (2006.01) |
| *A61K 9/00* | (2006.01) |
| *A61K 31/12* | (2006.01) |
| *A61K 31/337* | (2006.01) |
| *A61K 31/341* | (2006.01) |
| *A61K 31/351* | (2006.01) |
| *A61K 31/4196* | (2006.01) |
| *A61K 31/426* | (2006.01) |
| *A61K 31/435* | (2006.01) |
| *A61K 31/437* | (2006.01) |
| *A61K 31/453* | (2006.01) |
| *A61K 31/496* | (2006.01) |
| *A61K 31/506* | (2006.01) |
| *A61K 31/513* | (2006.01) |
| *A61K 47/10* | (2017.01) |
| *A61K 47/14* | (2017.01) |
| *A61K 47/34* | (2017.01) |
| *A61P 35/00* | (2006.01) |
| *A61K 45/06* | (2006.01) |

(52) U.S. Cl.
CPC .......... *A61K 9/1075* (2013.01); *A61K 9/0019* (2013.01); *A61K 9/107* (2013.01); *A61K 31/12* (2013.01); *A61K 31/337* (2013.01); *A61K 31/341* (2013.01); *A61K 31/351* (2013.01); *A61K 31/4196* (2013.01); *A61K 31/426* (2013.01); *A61K 31/435* (2013.01); *A61K 31/437* (2013.01); *A61K 31/453* (2013.01); *A61K 31/496* (2013.01); *A61K 31/506* (2013.01); *A61K 31/513* (2013.01); *A61K 47/10* (2013.01); *A61K 47/14* (2013.01); *A61K 47/34* (2013.01); *A61P 35/00* (2018.01); *A61K 45/06* (2013.01)

(58) Field of Classification Search
None
See application file for complete search history.

(56) References Cited

U.S. PATENT DOCUMENTS

| | | | | |
|---|---|---|---|---|
| 10,047,197 | B2* | 8/2018 | Sill | A61K 47/6907 |
| 2008/0299205 | A1* | 12/2008 | Mayer | A61K 47/593 |
| | | | | 424/489 |
| 2009/0192205 | A1* | 7/2009 | Augustijns | A61K 31/41 |
| | | | | 514/384 |
| 2017/0112800 | A1* | 4/2017 | Roy | A61K 47/554 |
| 2021/0252168 | A1* | 8/2021 | Zhan | A61P 35/00 |

FOREIGN PATENT DOCUMENTS

| | | |
|---|---|---|
| CN | 104083325 A | 10/2014 |
| CN | 108478531 A | 9/2018 |
| CN | 108619526 A | 10/2018 |

OTHER PUBLICATIONS

Abstract for Kwon ("Polymeric micelles for delivery of poorly water-soluble compounds", Crit Rev Ther drug Carrier Syst., vol. 20(5) (2003), p. 357-403) (Year: 2003).*
Vakil et al "Poly(Ethylene Glycol)-b-Poly(e-Caprolactone) and PEG-Phospholipid Form Stable Mixed Micelles in Aqueous Media" Langmuir vol. 22, pp. 9723-9729, 2006.
Dong et al. "Preparation and in vitro Anti-tumor Activity Evaluation of Folate-conjugated Polymeric Micelles Loaded with Doxorubicin", Chinese Journal of Pharmaceuticals, Dec. 31, 2011m No. 7, vol. 42, pp. 512-517.
Han et al. "9-NC-loaded folate-conjugated polymer micelles as tumor targeted drug delivery system: Preparation and evaluation in vitro", International Journal of Pharmaceutics, Jan. 4, 2009m vol. 372, pp. 125-131.

* cited by examiner

*Primary Examiner* — Sin J Lee
(74) *Attorney, Agent, or Firm* — Cesari & McKenna, LLP

(57) ABSTRACT

A pharmaceutical composition containing a mixed polymeric micelle and a drug enclosed in the micelle, in which the mixed polymeric micelle, 1 to 1000 nm in size, includes an amphiphilic block copolymer and a lipopolymer. Also disclosed are preparation of the pharmaceutical composition and use thereof for treating cancer.

12 Claims, 2 Drawing Sheets

PHARMACEUTICAL COMPOSITIONS CONTAINING MIXED POLYMERIC MICELLES

BACKGROUND

Mixed polymeric micelles have been extensively studied as effective vehicles for delivering poorly water-soluble drugs. Subjected to site-specific delivery, they can improve biopharmaceutical and pharmacokinetic properties of the drugs, thereby enhancing drug efficacy.

While conventional microparticles or nanoparticles are formed via a complicated emulsion process requiring use of surfactants for stabilization, mixed polymeric micelles less than 1 micrometer in size are typically prepared via a simplified self-assembling process that does not require surfactants or other agents for achieving stability.

Currently, mixed polymeric micelles are formed from various types of polymers, including copolymers and lipopolymers. For example, see Lee et al., *Journal of Controlled Release*, 2003, 91, 103-113, and Vakil et al., *Langmuir*, 2006, 22, 9723-9729. Compositions containing these polymeric micelles still need improvement in stability, drug loading, and encapsulation efficiency.

There is a need to develop mixed polymeric micelle-containing compositions that have improved properties.

SUMMARY

An aspect of the present invention is a method of preparing a pharmaceutical composition that unexpectedly exhibits high stability, high drug loading, and high encapsulation efficiency.

The method includes (i) providing starting materials containing an amphiphilic block copolymer, a lipopolymer, and a drug; (ii) mixing the starting materials in a solvent; (iii) removing the solvent to afford a dry film or a dry cake; (iv) adding water to solubilize the dry film or the dry cake to form a solution containing a mixed polymeric micelle; and (v) filtering the solution to provide a pharmaceutical composition.

In an embodiment of this method, the lipopolymer is conjugated with a ligand and the starting materials further include an additional lipopolymer not conjugated with a ligand.

Also within this scope of this invention are three related pharmaceutical compositions, each containing a mixed polymeric micelle and a drug enclosed in the micelle.

The first pharmaceutical composition is prepared by the method described above.

The second pharmaceutical composition contains a mixed polymeric micelle having a size of 1 to 1000 nm and a drug enclosed in the micelle. The mixed polymeric micelle includes an amphiphilic block copolymer and a lipopolymer conjugated with a ligand. The amphiphilic block copolymer has a hydrophilic segment and a hydrophobic segment, the lipopolymer has a hydrophilic polymer chain and a hydrophobic moiety covalently attached thereto, and the ligand is a targeting moiety conjugated to the hydrophilic polymer chain. Optionally, the mixed polymeric micelle further includes an additional lipopolymer that is not conjugated with a ligand.

The third pharmaceutical composition contains a mixed polymeric micelle having a size of 1 to 1000 nm and a drug enclosed in the micelle. The mixed polymeric micelle, having a drug loading of 10 to 45%, includes an amphiphilic block copolymer and a lipopolymer.

Further covered by this invention is a method for treating by administering to a subject in need thereof an effective amount of one of the three pharmaceutical compositions described above.

The details of the invention are set forth in the figures and description below. Other features, objects, and advantages of the invention will be apparent from the following detailed description of several embodiments, and also from the appending claims.

BRIEF DESCRIPTION OF THE FIGURES

The description below refers to the accompanying drawings, of which.

DETAILED DESCRIPTION

Figure 1:
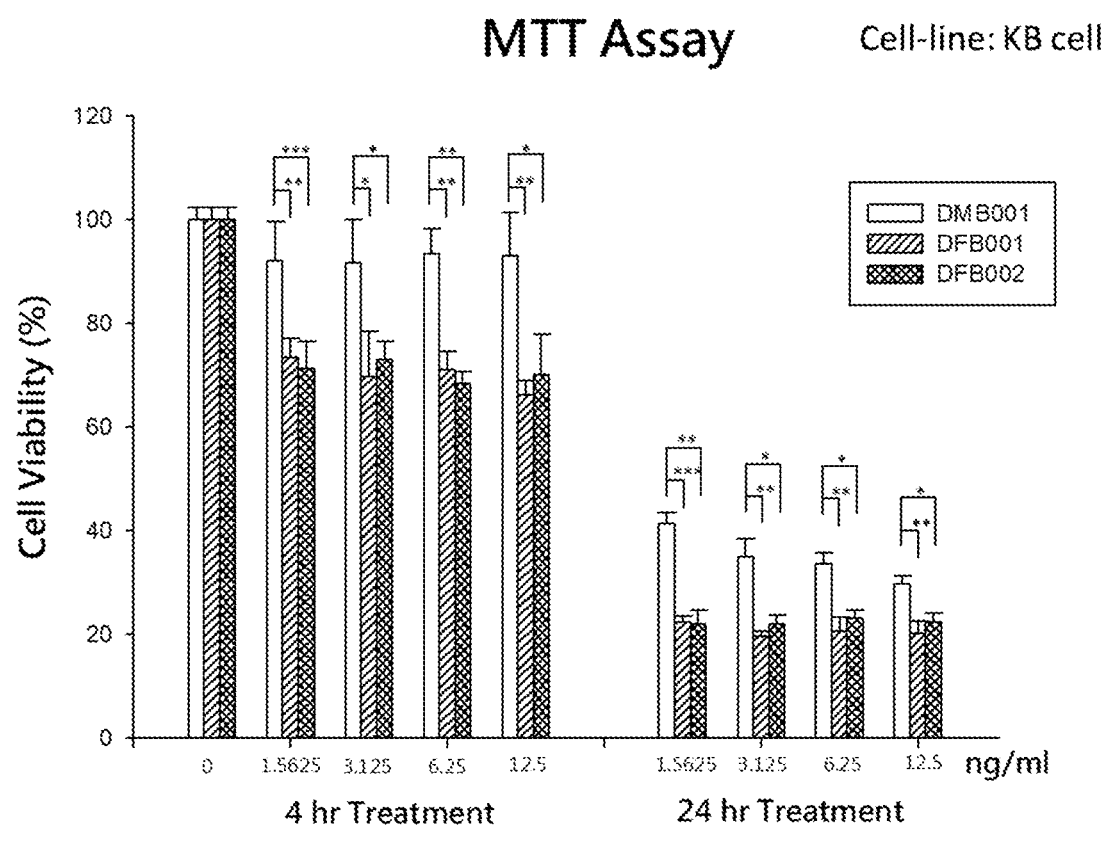
FIG. 1 is a bar graph showing viability of KB human epidermoid carcinoma cells after incubation for 4 hours and 24 hours in media containing four different pharmaceutical compositions of this invention at four different concentrations.

Described herein in detail are the first, second, and third pharmaceutical compositions set forth in the SUMMARY section above.

To facilitate discussion, the second pharmaceutical composition will be described first. It contains a mixed polymeric micelle and a drug enclosed in the micelle, in which the mixed polymeric micelle includes an amphiphilic block copolymer and a lipopolymer conjugated with a ligand. The mixed polymeric micelle has a size of 1 to 1000 nm (e.g., 30 to 500 nm).

The amphiphilic block copolymer has a hydrophilic segment and a hydrophobic segment. Examples of the hydrophilic segment include, but are not limited to, polyethylene glycol ("PEG"), methoxypolyethylene glycol ("mPEG"), hyaluronic acid, and poly-γ-glutamic acid. On the other hand, examples of the hydrophobic segment include, but are not limited to, polycaprolactone ("PCL"), polylactide, polyglycolide, poly(lactic-co-glycolic acid), polyvalerolactone, polybutyrolactone, polypropiolactone, polycarboxylate, and polydioxanone. An exemplary amphiphilic block copolymer has the hydrophilic segment being mPEG and the hydrophobic segment being PCL.

The lipopolymer includes a hydrophilic polymer chain and a hydrophobic moiety covalently attached thereto. High hydrophobicity of the hydrophobic moiety can greatly improve the stability, drug loading, and encapsulation efficiency of the mixed polymeric micelles. Examples of the lipopolymer include, but are not limited to, PEG-cholesterol, PEG-phospholipid, and PEG-diacylglycerol. An exemplary PEG-phospholipid is 1,2-distearoyl-sn-glycero-3-phosphoethanolamine-N-methoxy poly(ethylene glycol) ("PEG-DSPE").

The ligand is a targeting moiety conjugated to the hydrophilic polymer chain of the lipopolymer. Typically, the ligand is a macromolecule or a small molecule having a molecular weight of lower than 2000 daltons. The small molecule ligand, such as bombesin and bradykinin, can recognize a functional cell surface plasminogen activator.

An exemplary small molecule ligand is folate, N-acetyl histidine, or a peptide (e.g., an arginine-glycine-aspartic acid peptide and a peptide formed of 10-15 amino acids). Examples of the macromolecule ligand include, but are not limited to, an antibody, an antibody fragment, an aptamer, a prostate-specific membrane antigen ligand, and a growth factor (e.g., epidermal growth factor, platelet-derived growth factor, and vascular endothelial growth factor).

The drug contained in this pharmaceutical composition can be a therapeutic agent for treating cancer. Examples include, but are not limited to, cabazitaxel, paclitaxel, docetaxel, larotaxel, doxorubicin, doxorubicin hydrochloride, epirubicin, gemcitabine, letrozole, curcumin, temsirolimus, voriconazole, posaconazole, sirolimus, everolimus, ixabephilone, camptothecin, a camptothecin derivative, and a photosensitizer. In particular, cabazitaxel is the only taxane effective in treating docetaxel-resistant cancers known hitherto. It is generally associated with serious dose-limiting toxicity (e.g., neutropenia). A composition containing cabazitaxel in a mixed polymeric micelle greatly enhances the drug's biophysical properties (e.g., water solubility) and bioavailability. Note that a camptothecin derivative refers to a compound derived from and structurally close to camptothecin with improved pharmaceutical properties, e.g., solubility, metabolic stability, and biological potency. For example, see Zunino et al., *Current Pharmaceutical Design*, 2002, 8(27), 2505-2520.

Typically, the mixed polymeric micelle described above has a polydispersity index of 0.08 to 1.0, preferably lower than 0.33, and most preferably lower than 0.2. It can have a drug encapsulation efficiency of greater than 80%, preferably greater than 90%, and most preferably greater than 95%.

In one example, the mixed polymeric micelle further includes an additional lipopolymer not conjugated with a ligand. The lipopolymer can be, among others, PEG-cholesterol, PEG-phospholipid, PEG-vitamin E, and PEG-diacylglycerol. For instance, the PEG-phospholipid is PEG-DSPE.

In another example, the amphiphilic block copolymer is mPEG-PCL, the lipopolymer is PEG-DSPE, the ligand is folate or N-acetyl histidine, and the drug is cabazitaxel. The mixed polymeric micelle of such a composition has a size of 30 to 500 nm, a polydispersity index of lower than 0.33, and a drug encapsulation efficiency of greater than 90%.

In still another example, the mixed polymeric micelle includes an amphiphilic block copolymer that is mPEG-PCL; a ligand-conjugated lipopolymer that is ligand-PEG-DSPE, the ligand being folate or N-acetyl histidine; a lipopolymer that is PEG-DSPE; and a drug that is cabazitaxel. The mixed polymeric micelle of such a composition has a size of 30 to 500 nm, a polydispersity index of lower than 0.33, and a drug encapsulation efficiency of greater than 90%.

In a different example, the mixed polymeric micelle includes a lipopolymer conjugated with a ligand. The lipopolymer constitutes 4-25% (e.g., 5-15%) by weight of the mixed polymeric micelle. For a mixed polymeric micelle that includes a ligand-conjugated lipopolymer and a ligand-free lipopolymer, the two lipopolymers, together, constitute 4-25% (e.g., 5-15%) by weight of the mixed polymeric micelle.

Turning to the third pharmaceutical composition, it contains a mixed polymeric micelle, having a size of 1 to 1000 nm (e.g., 30 to 500 nm), and a drug enclosed in the micelle, in which the mixed polymeric micelle includes an amphiphilic block copolymer and a lipopolymer optionally conjugated with a ligand. The mixed polymeric micelle has a high drug loading of 10 to 45% (e.g., 15 to 40%). For example, the amphiphilic block copolymer is mPEG-PCL, the lipopolymer is PEG-DSPE, the drug is cabazitaxel, and the ligand is folate or N-acetyl histidine. Of note, when the lipopolymer is conjugated with a ligand, the mixed polymeric micelle can further include an additional lipopolymer not conjugated with a ligand.

Finally, the first pharmaceutical composition is prepared by the method set forth in the SUMMARY section above and described in greater detail below.

To reiterate, the method includes providing starting materials including an amphiphilic block copolymer, a lipopolymer, and a drug; mixing the starting materials in a solvent; removing the solvent to afford a dry film or a dry cake; adding water to solubilize the dry film or the dry cake to form a mixed polymeric micelle in which the drug is encapsulated; optionally sonicating the solution containing the mixed polymeric micelle; and filtering the solution to provide a pharmaceutical composition.

In an exemplary method, the lipopolymer includes a hydrophilic polymer chain and a hydrophobic moiety covalently attached to it. The lipopolymer also includes a ligand that is conjugated to the hydrophilic polymer chain. Notably, the starting materials can further include another lipopolymer. As an example, the starting materials include DSPE-PEG, in addition to mPEG-PCL; ligand-PEG-DSPE, the ligand being folate or N-acetyl histidine; and cabazitaxel.

In another exemplary method, the lipopolymer is not conjugated with a ligand. Preferably, the lipopolymer is PEG-DSPE, the amphiphilic block copolymer is mPEG-PCL, and the drug is cabazitaxel.

Still within the scope of this invention is a method of treating cancer using one of the three above-described pharmaceutical compositions. The method includes administering to a subject in need thereof an effective amount of one of the three pharmaceutical composition of this invention.

In certain embodiments of this method, the anti-cancer drug is cabazitaxel, the amphiphilic block copolymer is mPEG-PCL, and the lipopolymer is PEG-DSPE or folate-PEG-DSPE, in which the mixed polymeric micelle has a size of 30 to 500 nm, a polydispersity index of lower than 0.33, and a drug encapsulation efficiency of greater than 90%. In another embodiment, the mixed polymeric micelle contains both PEG-DSPE and folate-PEG-DSPE.

The cancer can be a solid tumor overexpressed with folate receptor. Examples of the solid tumor include, but are not limited to, lung cancer, ovarian tumor, breast cancer (e.g., metastatic breast cancer and triple negative breast cancer), endometrial cancer, uterus cancer, kidney cancer, brain cancer, head and neck cancer, hormone refractory metastatic prostate cancer, bladder cancer, stomach cancer (e.g., metastatic stomach cancer), transitional cell carcinoma, and liposarcoma.

The term "treating" or "treatment" herein refers to administering a pharmaceutical composition described above to a subject, who has an above-described disease, i.e., cancer, a symptom of such a disease, or a predisposition toward such a disease, with the purpose of conferring a therapeutic or prophylactic effect. The term "an effective amount" refers to the amount of an active drug that is required to confer such effect. Effective doses will vary, as recognized by those skilled in the art, depending on the types of disease treated, route of administration, excipient usage, and the possibility of co-usage with other therapeutic treatment.

A pharmaceutical composition of this invention can be administered via various routes, such as parenteral administration, e.g., subcutaneous, intracutaneous, intravenous, intraperitoneal, intramuscular, intraarticular, intraarterial, intrasynovial, intrasternal, intrathecal, intralesional, and intracranial injection.

A sterile injectable pharmaceutical composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All of the publications cited herein are incorporated by reference.

EXAMPLE 1

Preparation of a Folate-Conjugated Lipopolymer

A folate-conjugated lipopolymer was prepared following protocols reported in Cho et al., *Journal of Nanomaterials*, 2015, 16(1), Article No. 36.

More specifically, to prepare a folate-conjugated lipopolymer, 25 mg of folate was dissolved in 1 mL of dimethyl sulfoxide ("DMSO") and 100 mg of amino-substituted 1,2-distearoyl-sn-glycero-3-phosphoethanolamine-N-methoxy poly(ethylene glycol) ("DSPE-PEG$_{5k}$-NH$_2$") was dissolved in 0.5 mL of pyridine containing 32.5 mg of N,N'-dicyclohexyl-carbodiimide ("DCC"). The two solutions thus formed were mixed and left to stand at room temperature for 4 hours. Pyridine was subsequently removed by rotary vacuum evaporation. To the mixture, 3 mL of water was added and the insoluble materials were removed by centrifugation at 36,000 g for 15 minutes. The supernatant thus obtained was dialyzed in Spectra/Por CE for 24 hours against saline and then for 24 hours against water. The dialyzed product, i.e., folate-PEG$_{5k}$-DSPE, was lyophilized and stored at −20° C. before use. Note that the subscript "5k" indicates the molecular weight of the polymer, i.e., an average $M_n$ of 5,000.

The folate-conjugated lipopolymer thus obtained was used to prepare mixed polymeric micelles containing cabazitaxel and mPEG$_{5k}$-b-PCL$_{2k}$.

EXAMPLE 2

Preparation and Characterization of Folate-Conjugated Cabazitaxel-Loaded Mixed Polymeric Micelles Three pharmaceutical compositions, each containing a different folate-conjugated cabazitaxel-loaded mixed polymeric micelle ("CBZ-mPM"), were prepared following the protocols reported in Cho et al., *Journal of Nanomaterials*, 2015, 16(1), Article No. 36, and Vakil et al., *Langmuir*, 2006, 22, 9723-9729.

First, a mixture was prepared by dissolving block copolymer mPEG$_{5k}$-b-PCL$_{2k}$ (10 mg), folate-PEG$_{5k}$-DSPE (0.46, 0.97, or 2.20 mg), and cabazitaxel (5 mg) in 1 mL of tetrahydrofuran ("THF") at 60° C. Subsequently, THF was removed by rotary evaporation to obtain a dry film or a dry cake. Water was then added to solubilize the dry film or the dry cake at room temperature, thereby forming spontaneously a folate-conjugated CBZ-mPM during the solubilization process. Further, the solution was sonicated at room temperature for 5 minutes to reduce the particle size of the resultant micelle and narrow the size distribution thereof. Finally, a pharmaceutical composition was obtained by filtration using a filter of 0.22 μm polyvinylidene difluoride ("PVDF") membrane to remove un-encapsulated cabazitaxel.

Shown in Table 1 below is the characterization data for three exemplary folate-conjugated CBZ-mPMs, i.e., DFB001, DFB002, and DFB003, and two CBZ-mPMs without folate, i.e., DMB001 and DMB002. Note that DMB001 and DMB002 were prepared following the protocols described above, in which folate-PEG$_{5k}$-DSPE was replaced with a lipopolymer not conjugated with folate, i.e., PEG$_{5k}$-DSPE. A cabazitaxel-loaded non-mixed polymeric micelle ("CBZ-PM"), i.e., DB003, was included as a reference.

The five CBZ-mPMs and the one CBZ-PM were characterized by five parameters, i.e., particle size, polydispersity index, cabazitaxel concentration, drug loading, and encapsulation efficiency. Particle size and polydispersity index ("PDI") were obtained with a laser particle size analyzer (Beckman Delsa™Nano S). The quantity of encapsulated cabazitaxel in each CBZ-mPM was determined by HPLC. Drug-to-polymer weight % ("DIP weight %"), drug loading ("DL"), and encapsulation efficiency ("EE") were calculated according to the following formulas:

D/P weight %=mass of drug/mass of total polymer (mPEG-PCL+lipopolymer)×100%

DL (%)=mass of drug in micelle/mass of total polymer and drug in micelle×100%

EE (%)=mass of drug after filtration/mass of drug before filtration×100%

Referring back to Table 1, "A" represents mPEG$_{5k}$-b-PCL$_{2k}$, "B" represents PEG$_{5k}$-DSPE, "C" represents folate-PEG$_{5k}$-DSPE, and "size" refers to particle size. "CBZ", "PDI", again, refer to cabazitaxel and polydispersity index, respectively. By extension, the two CBZ-mPMs that contained PEG$_{5k}$-DSPE, i.e., DMB001 and DMB002, are denoted as "AB", while the CBZ-mPMs that contained folate-PEG$_{5k}$-DSPE, i.e., DFB001, DFB002, and DFB003, are denoted as "AC".

TABLE 1

Characterization of CBZ-mPMs

| | Code | A (mg/mL) | B (mg/mL) | C (mg/mL) | B/A or C/A weight ratio (%) | CBZ (mg/mL) | D/P weight (%) | Size (nm) | PDI | CBZ Conc. (mg/ml) | DL (%) | EE (%) |
|---|---|---|---|---|---|---|---|---|---|---|---|---|
| non-mixed | DB003 | 10 | — | — | — | 5 | 50.0 | 80.0 | 0.220 | 3.480 | 25.8 | 72.5 |
| AB | DMB001 | 10 | 0.41 | — | 4.1 | 5 | 48.0 | 108.0 | 0.329 | 4.547 | 30.4 | 92.9 |
| | DMB002 | 10 | 0.41 | | 4.1 | 6 | 57.6 | 84.3 | 0.260 | 5.832 | 35.9 | 99.6 |
| AC | DFB001 | 10 | — | 0.46 | 4.6 | 5 | 47.8 | 74.3 | 0.336 | 4.580 | 30.5 | 97.7 |
| | DFB002 | 10 | — | 0.97 | 9.7 | 5 | 45.6 | 72.0 | 0.350 | 4.450 | 28.9 | 98.0 |
| | DFB003 | 10 | — | 2.20 | 22.0 | 5 | 41.0 | 117.3 | 0.373 | 4.376 | 26.4 | 97.2 |

As shown in Table 1, each of the five CBZ-mPMs exhibited a drug loading of about 50% and an encapsulation efficiency of greater than 90%. On the other hand, the CBZ-PM, i.e., DB003, had a drug loading of 50% and an encapsulation efficiency of only 72.5%. In other words, the five CBZ-mPMs all exhibited higher encapsulation efficiencies than the CBZ-PM, while drug loading was comparable for all six micelles.

These results indicate that the CBZ-mPMs of this invention unexpectedly have very high encapsulation efficiencies.

EXAMPLE 3

In Vitro Anti-Tumor Activity of CBZ-mPMs

A study was performed to evaluate in vitro anti-tumor activity of three of the five CBZ-mPMs described in EXAMPLE 2, i.e., DMB001, DFB001, and DFB002.

An MTT assay (MTT representing 3-(4,5-dimethylthiazol-2-yl)-2,5-diphenyltetrazolium bromide) was conducted following the protocols reported in Chan et al., *Biomaterials*, 2009, 30, 1627-1634, and Kumar et al., *Biomaterials*, 2012, 33, 1180-1189.

More specifically, KB human epidermoid carcinoma cells were grown in RPMI-1640 medium supplemented with 10% fetal bovine serum ("FBS"), 100 units/mL penicillin, and 100 mg/mL streptomycin under 5% $CO_2$ at 37° C. The KB cells were seeded in a 96-well plate in 200 mL medium per well at a density of 15,000 cells/well for 24 hours. The medium was then replaced with 200 mL of medium containing DMB001, DFB001, or DFB002 at four different concentrations (i.e., 1.5625, 3.125, 6.25, and 12.5 ng/mL) and incubated for 4 hours and 24 hours with 5% $CO_2$ at 37° C. before running the assays. The CBZ-mPM-containing media were then removed to avoid interference in the assays. A 0.5 mg/mL MTT solution in medium was added and cells were incubated for another 4 hours. The MTT containing media were removed and cells were rinsed three times with phosphate-buffered saline. 200 mL of DMSO was then added to lyse the cells and the resulting mixture was incubated at room temperature for 30 minutes. Absorbance at 570 nm for each well was measured on an ELISA Reader. Viability of the non-treated control cells was calculated to be 100%. Cell viability (%) was calculated according to the following formula ("OD" denotes optical density):

Cell viability (%)=(OD570 nm of sample–OD of blank sample)/OD570 nm control×100%

As shown in FIG. 1, all three tested CBZ-mPMs exhibited strong in vitro anti-tumor activity at the four tested dosages after treatment for 24 hours.

Unexpectedly, the two AC CBZ-mPMs, i.e., DFB001 and DFB002, exhibited much higher anti-tumor activities against folate receptor-overexpressed KB tumor cells in both 4-hour and 24-hour treatments, as compared with the AB CBZ-mPM, i.e., DMB001. More specifically, in the 4-hour treatment, the KB cells treated with DMB001 at the four different concentrations (i.e., 1.5625, 3.125, 6.25, and 12.5 ng/mL) had a cell viability of about 90%, compared with about 70% exhibited by DFB001 or DFB002; and in the 24-hour treatment, the KB cells treated with DMB001 at the same concentrations had cell viabilities of 35-45%, compared to about 20% exhibited by DFB001 or DFB002. Clearly, the enhancement of anti-tumor activity was attributable to use of folate as the ligand in DFB001 and DFB002, which was not present in DMB001.

These results indicate that CBZ-mPMs of this invention unexpectedly have high efficacy in treating cancer at low dosages.

EXAMPLE 4

Preparation and Characterization of CBZ-mPMs Containing PEGsk-DSPE, Folate-PEG$_{5k}$-DSPE, or both PEG$_{5k}$-DSPE and folate-PEG$_{5k}$-DSPE Eight exemplary CBZ-mPMs that contained PEG$_{5k}$-DSPE, folate-PEG$_{5k}$-DSPE, or both PEG$_{5k}$-DSPE and folate-PEG$_{5k}$-DSPE were prepared following the procedure described in EXAMPLE 2.

More specifically, mPEG$_{5k}$-b-PCL$_{2k}$ (20 mg), folate-PEG$_{5k}$-DSPE (0-2 mg), PEG$_{5k}$-DSPE (0-3 mg), and cabazitaxel (4 mg) were dissolved in 1 mL chloroform/methanol (9:1 v/v) at 60° C. The solvent was subsequently removed by rotary evaporation to obtain a dry film or a dry cake. Water was then added to solubilize the dry film or the dry cake at room temperature, thereby forming spontaneously a CBZ-mPM during the solubilization process. Further, sonication was performed at room temperature for 5 minutes to reduce the particle size of the resultant micelle and narrow the size distribution thereof. Finally, a pharmaceutical composition was obtained by filtration using a filter of 0.22 μm PVDF membrane to remove un-encapsulated cabazitaxel.

Shown in Table 2 below is the characterization data for the eight exemplary CBZ-mPMs and a CBZ-PM, i.e., DB005, included as a reference. Among the eight exemplary CBZ-mPMs, three of them, i.e., DMB022, DMB023, DMB025, contained PEG$_{5k}$-DSPE; two of them, i.e. DFB008 and DFB012, contained folate-PEG$_{5k}$-DSPE; and three of them, i.e., DFB009, DFB010, and DFB014, contained both PEG$_{5k}$-DSPE and folate-PEG$_{5k}$-DSPE.

All of the eight exemplary CBZ-mPMs and the CBZ-PM were characterized by five parameters, i.e., particle size, polydispersity index, cabazitaxel concentration, drug loading, and encapsulation efficiency. Particle size and PDI were obtained with a laser particle size analyzer (Beckman Delsa™Nano S). The quantity of encapsulated cabazitaxel in each micelle was determined by HPLC. Encapsulation efficiencies and drug loadings were calculated using the formulas provided in EXAMPLE 2.

In Table 2, the three CBZ-mPMs that contained both $PEG_{5k}$-DSPE and folate-$PEG_{5k}$-DSPE, i.e., DFB009, DFB010, and DFB014, are denoted as "ABC". For the definitions of "A," "B", "C", "CBZ", "size", "PDI", "DL", "EE", "AB", and "AC", see EXAMPLE 2.

TABLE 2

Characterization of AB, AC, and ABC CBZ-mPMs

|  |  | Composition | | | | | Characterization | | | | |
|---|---|---|---|---|---|---|---|---|---|---|---|
|  |  |  |  |  |  |  |  |  | CBZ | | |
|  | Code | A (mg/mL) | B (mg/mL) | C (mg/mL) | B + C (wt %) | CBZ (mg/mL) | Size (nm) | PDI | Conc. (mg/mL) | DL (%) | EE (%) |
| non-mixed | DB005 | 20 | — | — | — | 4 | 45.5 | 0.199 | 4.60 | 18.7 | 95.3 |
| AB | DMB022 | 20 | 1 | — | 5 | 4 | 44.3 | 0.113 | 4.43 | 17.4 | 90.0 |
|  | DMB023 | 20 | 2 | — | 10 | 4 | 41.2 | 0.083 | 4.27 | 16.3 | 95.3 |
|  | DMB025 | 20 | 3 | — | 15 | 4 | 43.0 | 0.166 | 4.13 | 15.2 | 96.5 |
| AC | DFB008 | 20 | — | 1 | 5 | 4 | 45.7 | 0.231 | 4.39 | 17.3 | 90.3 |
|  | DFB012 | 20 | — | 2 | 10 | 4 | 56.5 | 0.271 | 4.15 | 15.9 | 94.9 |
| ABC | DFB009 | 20 | 1 | 1 | 10 | 4 | 43.2 | 0.135 | 4.14 | 15.8 | 89.2 |
|  | DFB010 | 20 | 2 | 1 | 15 | 4 | 45.1 | 0.224 | 3.72 | 13.9 | 93.5 |
|  | DFB014 | 20 | 1 | 2 | 15 | 4 | 45.5 | 0.228 | 4.30 | 15.8 | 90.5 |

As shown in Table 2, with the exception of DFB012, which had a particle size of 56.5 nm, the CBZ-mPMs and the CBZ-PM had similar particle sizes (all within the range of 41-46 nm). Further, for each of the nine micelles, PDI was smaller than 0.3 and EE was ~90% or higher.

These results show that CBZ-mPMs of this invention unexpectedly have high encapsulation efficiencies and narrow size distributions.

EXAMPLE 5

Storage Stability of CBZ-mPMs

The eight CBZ-mPMs and the CBZ-PM described in Example 4 were stored in water at 25° C. for a period of 6 days (144 hours). Particle size was measured with a laser particle size analyzer (Beckman Delsa™Nano S) to monitor the storage stability. The stability data thus obtained is shown in Table 3.

TABLE 3

Storage stability of CBZ-mPMs in water at 25° C.

|  | Code | 0 hr Size (nm) | 24 hr Size (nm) | 96 hr Size (nm) | 144 hr Size (nm) | Stability (hr) |
|---|---|---|---|---|---|---|
| non-mixed | DB005 | 45.5 | p* | p | p | <24 |
| AB | DMB022 | 44.3 | 44.2 | 42.3 | p | 96~144 |
|  | DMB023 | 41.2 | 39.4 | 40.4 | p | 96~144 |
|  | DMB025 | 43.0 | 41.4 | 41.1 | 39.2 | >144 |
| AC | DFB008 | 45.7 | 43.6 | 43.1 | p | 96~144 |
|  | DFB012 | 56.5 | 42.2 | 42.8 | p | 96~144 |
| ABC | DFB009 | 43.2 | 43.5 | 40.9 | p | 96~144 |
|  | DFB010 | 45.1 | 44.7 | 39.8 | 38.8 | >144 |
|  | DFB014 | 45.5 | 44.8 | 45.4 | 55.4 | >144 |

*p = precipitation

As shown in Table 3, the CBZ-PM, i.e., DB005, was stable in water at 25° C. for less than 24 hours. By contrast, all eight exemplary CBZ-mPMs were stable under the same storage condition for longer than 96 hours. In particular, DFB012, DFB010, and DFB014, all containing 15% lipopolymer by weight (see Table 2, column 6), were most stable.

These results show that storage stability of CBZ-mPMs of this invention is unexpectedly high. They also show that CBZ-mPM storage stability can be enhanced by increasing the amount of lipopolymer contained in the micelle.

Further, serum stability of the eight exemplary CBZ-mPMs, as well as that of reference sample DB005, was evaluated by measuring changes in turbidity over a period of 96 hours. An increase in turbidity indicated particle aggregation caused by nonspecific interactions with the serum proteins (Z.-X. Zhao et al., Biomaterials, 2012, 33, 6793-6807).

Specifically, aqueous solutions of the eight CBZ-mPMs and an aqueous solution of DB005 (100 μl) were individually mixed with the same volume of FBS (100 μl) in centrifuge tubes. The resulting solution mixtures were subsequently incubated at 37° C.

Aggregation induced by serum was measured in terms of turbidity by determining the absorbance values at 630 nm wavelength at different time points (i.e., 0 hr, 24 hrs, and 96 hrs). phosphate-buffered saline ("PBS") was used as a blank solution. The results thus obtained are shown in Table 4 below.

TABLE 4

Serum stability of CBZ-mPMs at 37° C.

|  | Code | 0 hr Turbidity (%) | 24 hr Turbidity (%) | 96 hr Turbidity (%) | Stability (hr) |
|---|---|---|---|---|---|
| non-mixed | DB005 | 0.4 | 20.8 | p* | 24~96 |
| AB | DMB022 | 0.2 | 0.7 | p | 24~96 |
|  | DMB023 | 0.2 | 0.7 | 24.6 | >96 |
|  | DMB025 | 0.2 | 0.7 | 18.1 | >96 |
| AC | DFB008 | 0.8 | 1.4 | 6.0 | >96 |
|  | DFB012 | 1.8 | 4.3 | p | 24~96 |
| ABC | DFB009 | 0.5 | 1.0 | 18.9 | >96 |
|  | DFB010 | 0.6 | 0.8 | 5.6 | >96 |
|  | DFB014 | 0.7 | 0.8 | 12.6 | >96 |

*p = precipitation

As shown in Table 4, turbidity of the solution containing the CBZ-PM, i.e. DB005, significantly increased after incubation at 37° C. for 24 hours and the CBZ-PM precipitated after between 24-96 hours. Solutions containing the CBZ-mPMs, on the other hand, did not experience the same increase in turbidity after incubation for 24 hours. Further, six of the eight CBZ-mPMs tested, i.e., DMB023, DMB025, DFB008, DFB009, DFB010, and DFB014, were clearly more stable in than the CBZ-PM. Indeed, they remained in solution after being incubated for 96 hours. Unexpectedly, CBZ-mPMs that contained both $PEG_{5k}$-DSPE and folate-$PEG_{5k}$-DSPE exhibited higher serum stability as compared to CBZ-mPMs that contained only folate-$PEG_{5k}$-DSPE.

These results indicate that CBZ-mPMs of this invention unexpectedly have enhanced storage stability and serum stability.

EXAMPLE 6

In Vivo Anti-Tumor Activity of DFB014

In vivo anti-tumor activity of DFB014 was studied in female athymic nude mice (nu/nu, body weight=20~25 g). The mice were subcutaneously implanted with a human epidermal carcinoma xenograft cell line, KB cells ($2\times10^7$ cells per animal), which overexpresses folate receptors. After implantation, tumors were allowed to grow for 28 days to reach volume ~350 mm³, followed by administration of a single dose of Jevtana (trade name of cabazitaxel) or DFB014 (an equivalent dose of cabazitaxel=10 mg/kg) suspended in PBS to the tail veins of the mice at day 0. At predetermined time points, a major axis and a minor axis of tumors were measured using a caliper. Tumor volume was then calculated using the formula: $(3/4)\pi a^2 b$, where a and b are the length of the minor and major axis of a tumor, respectively.

In turn, tumor volume was used to determine the tumor growth inhibition rate % ("TGI") of Jevtana and DFB014 according to the formula:

$$TGI=(V_{Tm}-V_{T0})*100\%/V_{T0},$$

in which $V_{Tm}$ is tumor volume at a predetermined time point and $V_{T0}$ is tumor volume at day 0, i.e., the day of Jevtana/DFB014 administration.

Figure 2:
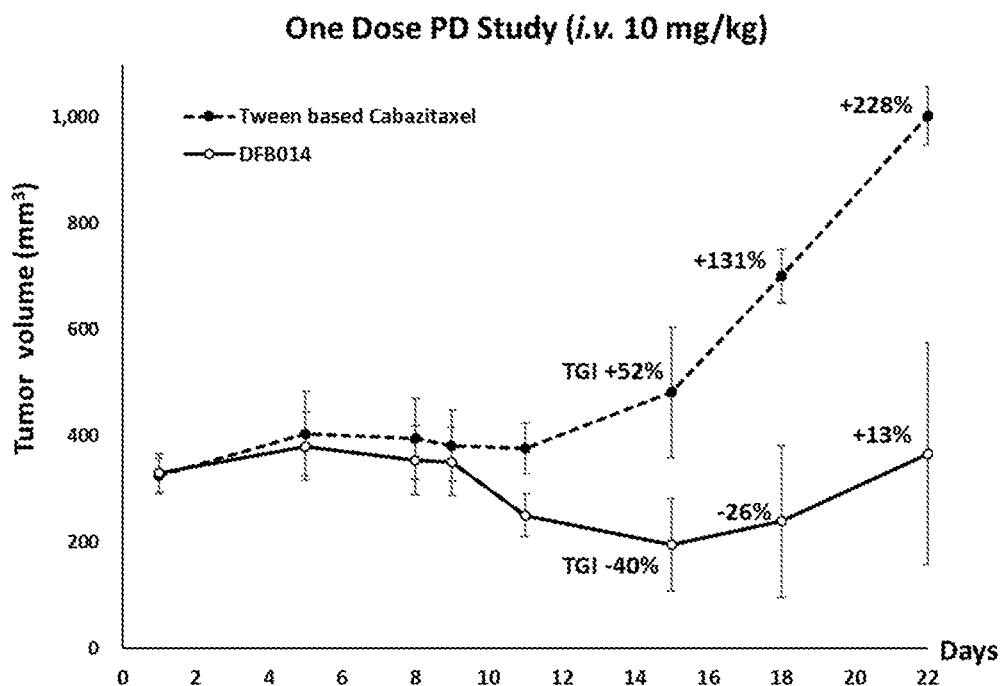
FIG. 2 is a plot showing tumor volume in tumor-bearing mice over a 22-day period after administration of a pharmaceutical composition of this invention or Jevtana.

FIG. 2 shows the change in tumor volume over a period of 22 days of a tumor treated with Jevtana and a tumor treated with DFB014. For the tumor treated with Jevtana, tumor volume remained consistent from day 0 to day 11, but it noticeably increased starting from day 12. The TGI of Jevtana was 52% on day 15, 131% on day 18, and 228% on day 22.

By contrast, the tumor treated with DFB014, which remained consistent in volume from day 0 to day 9, decreased in size from day 10 to day 15 before expanding in volume. The TGI of DFB014 was ~40% on day 15 (the negative value indicating tumor shrinkage), ~26% on day 18, and 13% on day 22, which were significantly lower than the TGI of Jevtana at the same time points. This result indicates that anti-tumor activity of DFB014 was significantly higher than that of Jevtana.

EXAMPLE 7

In Vivo Tumor Targeting of CBZ-mPMs

To investigate in vivo tumor targeting of CBZ-mPMs by fluorescence imaging, a near IR dye, i.e., Cy5.5, was co-loaded into two exemplary CBZ-mPMs, i.e., DMB025 (which does not contain folate) and DFB014 (which contains folate), to prepare two Cy5.5-containing CBZ-mPMs, i.e., CyDMB025 and CyDFB014. Specifically, the two Cy5.5-containing CBZ-mPMs were prepared according to the protocol described in EXAMPLE 4, with the addition of Cy5.5 to the starting materials.

Shown in Table 5 below is the characterization data for the two Cy5.5-containing CBZ-mPMs. Both of the CBZ-mPMs were characterized by four parameters, i.e., particle size, polydispersity index, Cy5.5 concentration, and cabazitaxel concentration. Particle size and PDI were obtained with a laser particle size analyzer (Beckman Delsa™Nano S). The quantity of encapsulated Cy5.5 and that of encapsulated cabazitaxel in each CBZ-mPM were determined by HPLC. For the definitions of "A," "B", "C", "CBZ", "size", and "PDI", see EXAMPLE 2.

TABLE 5

Characterization of CBZ-mPMs co-loaded with Cy5.5

| | Composition | | | | | | Characterization | | | |
|---|---|---|---|---|---|---|---|---|---|---|
| Code | A (mg/mL) | B (mg/mL) | C (mg/mL) | B + C (wt %) | Cy5.5 (mg/mL) | CBZ (mg/mL) | Size (nm) | PDI | Cy5.5 Conc. (mg/mL) | CBZ Conc. (mg/mL) |
| CyDMB025 | 20 | 3 | — | 15 | 0.25 | 4 | 56.2 | 0.270 | 0.253 | 3.647 |
| CyDFB014 | 20 | 1 | 2 | 15 | 0.25 | 4 | 55.4 | 0.231 | 0.232 | 3.652 |

Tumor targeting of the two Cy5.5-containing CBZ-mPMs was studied in female athymic nude mice (nu/nu, body weight=20-25 g). The mice were subcutaneously implanted with a human epidermal carcinoma xenograft cell line, KB cells ($2\times10^7$ cells per animal). After implantation, tumors were allowed to grow for 28 days to reach volume ~350 mm³. The mice were then injected via tail vein with CyDMB025 or CyDFB014 such that a total of 2 nmol of Cy5.5 was administered. Subsequently, the mice were anesthetized with 2% isoflurane before fluorescence imaging at various time points. In vivo fluorescence imaging was performed with an IVIS three-dimensional imaging system.

Figure 3:
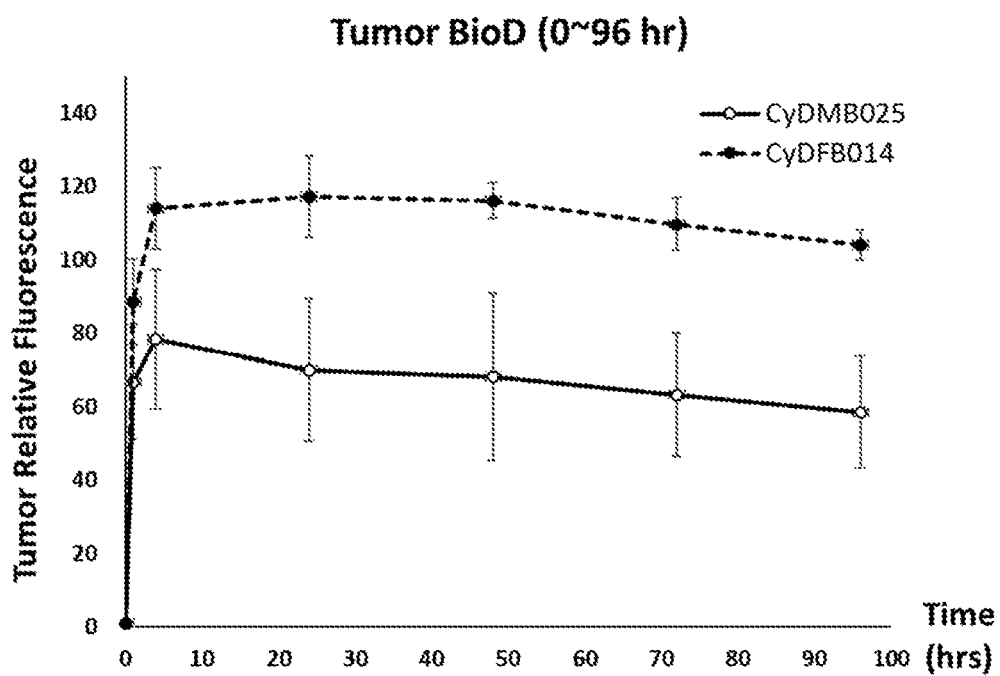
FIG. 3 is a plot showing relative fluorescence versus day in tumors of mice treated with pharmaceutical compositions of this invention that were co-loaded with Cy5.5.

FIG. 3 is a plot of relative fluorescence as a function of time in KB tumors of mice treated with CyDMB025 and of those treated with CyDFB014. As shown in the figure, both Cy5.5-containing CBZ-mPMs gradually accumulated into the KB tumors within ~4 hours. Importantly, relative tumor fluorescence was consistently higher in mice injected with CyDFB014 than in mice injected with CyDMB025, indicating that CyDFB014 accumulated in the KB tumors more effectively. This advantage was attributable to the folate ligand in CyDFB14, which allowed the CBZ-mPM to target folate-receptor overexpressing tumors.

The results from this study show that CyDFB14 exhibited enhanced tumor targeting.

film or a dry cake. Water was then added to solubilize the dry film or the dry cake at room temperature, thereby spontaneously forming DHB001 during the solubilization process. Finally, a pharmaceutical composition was obtained by filtration using a filter of 0.22 μm PVDF membrane to remove un-encapsulated cabazitaxel.

Shown in Table 6 below is the characterization data for DHB001. It was characterized by five parameters, i.e., particle size ("size"), polydispersity index ("PDI"), cabazitaxel ("CBZ") concentration, drug loading ("DL"), and encapsulation efficiency ("EE"). The particle size and PDI were obtained with a laser particle size analyzer (Beckman Delsa™Nano S). The quantity of encapsulated cabazitaxel in DHB001 was determined by HPLC. The EE and drug loading and were calculated using the formula provided in EXAMPLE 2.

In Table 6, "C" represents NAcHis-PEG$_{5k}$-DSPE and "size", "PDI", "CBZ", "DL", and "EE" are as defined in the preceding paragraph. For the definitions of "A" and "B", see EXAMPLE 2.

TABLE 6

Characterization of NAcHis-conjugated CBZ-mPMs

| | Composition | | | | Characterization | | | | |
|---|---|---|---|---|---|---|---|---|---|
| | | | | | | CBZ | | | |
| Code | A (mg/mL) | B (mg/mL) | C (mg/mL) | B + C (wt %) | CBZ (mg/mL) | Size (nm) | PDI | Conc. (mg/mL) | DL (%) | EE (%) |
| DHB001 | 20 | 1 | 2 | 15 | 5 | 38.7 | 0.22 | 4.72 | 17.0 | >99 |

EXAMPLE 8

Preparation of an N-acetyl-histidine-Conjugated Lipopolymer

An N-acetyl-histidine-conjugated lipopolymer was prepared following a procedure adapted from that described in EXAMPLE 1.

More specifically, 25 mg of DSPE-PEG$_{5k}$-NH$_2$, 4.93 mg of N-acetyl histidine ("NAcHis"), 5.2 mg of DCC, 2.9 mg of N-hydroxy succinimide ("NHS"), and 3.1 mg of 4-dimethylamino-pyridine ("DMAP") were dissolved in 0.4 mL of anhydrous DMSO. The mixture was stirred at room temperature for 48 hours. Subsequently, 2.5 mL of DMSO was added to the mixture, followed by repeated filtrations to remove dicyclohexylcarbodiurea, a byproduct. The filtrate was then dialyzed (molecular weight cut-off 3500) against DMSO for 3 days to remove residual NAcHis, NHS, and DMAP. The final product, i.e., NAcHis-PEG$_{5k}$-DSPE, was obtained by lyophilization.

EXAMPLE 9

Preparation and Characterization of an N-acetyl-histidine-Conjugated CBZ-mPM

DHB001, a CBZ-mPM containing PEG$_{5k}$-DSPE and NAcHis-PEG$_{5k}$-DSPE, was prepared by adapting the procedure described in EXAMPLE 4.

More specifically, a mixture was first prepared by dissolving mPEG$_{5k}$-b-PCL$_{2k}$ (20 mg), NAcHis-PEG$_{5k}$-DSPE (2 mg), PEG$_{5k}$-DSPE (1 mg), and cabazitaxel (4 mg) in 1 mL chloroform/methanol (9:1 v/v) at 60° C. The solvent was subsequently removed by rotary evaporation to obtain a dry As shown by the results in Table 6, DHB001, like the other CBZ-mPMs of this invention, unexpectedly exhibited a high encapsulation efficiency and a narrow size distribution.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A pharmaceutical composition comprising a mixed polymeric micelle having a size of 1 to 1000 nm and a drug enclosed in said micelle, wherein the mixed polymeric micelle contains an amphiphilic block copolymer and a first lipopolymer conjugated with a ligand, in which the amphiphilic block copolymer has one hydrophilic segment and one hydrophobic segment, the first lipopolymer is polyethylene glycol ("PEG")-cholesterol, PEG-phospholipid, PEG-vitamin E, or PEG-diacylglycerol, the first lipopolymer constitutes 4-25% by weight of the mixed polymeric micelle, and the ligand is a targeting moiety conjugated to the PEG chain of the first lipopolymer, wherein the hydrophilic segment of the amphiphilic block copolymer is PEG or methoxypolyethylene glycol ("mPEG") and the hydrophobic segment of the amphiphilic block copolymer is polycaprolactone ("PCL"), polyvalerolactone, polybutyrolactone, or polypropiolactone.

2. The pharmaceutical composition of claim 1, wherein the ligand is folate, N-acetyl histidine, a peptide, an antibody, an antibody fragment, an aptamer, a prostate-specific membrane antigen ligand, or a growth factor selected from the group consisting of epidermal growth factor, platelet-derived growth factor, and vascular endothelial growth factor.

3. The pharmaceutical composition of claim 2, wherein the ligand is folate or N-acetyl histidine.

4. The pharmaceutical composition of claim 1, wherein the drug is cabazitaxel, paclitaxel, docetaxel, larotaxel, doxorubicin, doxorubicin hydrochloride, epirubicin, gemcitabine, letrozole, curcumin, temsirolimus, voriconazole, posaconazole, sirolimus, everolimus, ixabephilone, camptothecin, or a camptothecin derivative.

5. The pharmaceutical composition of claim 4, wherein the drug is cabazitaxel.

6. The pharmaceutical composition of claim 1, wherein the hydrophilic of the amphiphilic block copolymer segment is mPEG and the hydrophobic segment of the amphiphilic block copolymer is PCL.

7. The pharmaceutical composition of claim 1, wherein the PEG-phospholipid is 1,2-distearoyl-sn-glycero-3-phosphoethanolamine-N-methoxy poly(ethylene glycol) ("PEG-DSPE").

8. The pharmaceutical composition of claim 1, wherein the amphiphilic block copolymer is mPEG-PCL, the first lipopolymer is PEG-DSPE, the ligand is folate or N-acetyl histidine, and the drug is cabazitaxel.

9. A method of treating cancer, the method comprising administering to a subject in need thereof an effective amount of the pharmaceutical composition of claim 1.

10. A pharmaceutical composition, comprising a mixed polymeric micelle having a size of 1 to 1000 nm and a drug enclosed in said micelle, wherein the mixed polymeric micelle contains an amphiphilic block copolymer, a first lipopolymer conjugated with a ligand, and a second lipopolymer not conjugated with a ligand, in which the amphiphilic block copolymer has one hydrophilic segment and one hydrophobic segment, the first lipopolymer is polyethylene glycol ("PEG")-cholesterol, PEG-phospholipid, PEG-vitamin E, or PEG-diacylglycerol, the first lipopolymer and the second lipopolymer, together, constitutes 4-25% by weight of the mixed polymeric micelle, and the ligand is a targeting moiety conjugated to the PEG chain of the first lipopolymer, wherein the hydrophilic segment of the amphiphilic block copolymer is PEG or methoxypolyethylene glycol ("mPEG") and the hydrophobic segment of the amphiphilic block copolymer is polycaprolactone ("PCL"), polyvalerolactone, polybutyrolactone, or polypropiolactone.

11. The pharmaceutical composition of claim 10, wherein the second lipopolymer is PEG-cholesterol, PEG-phospholipid, PEG-vitamin E, or PEG-diacylglycerol.

12. The pharmaceutical composition of claim 11, wherein the amphiphilic block copolymer is mPEG-PCL, each of the first lipopolymer and the second lipopolymer is PEG-DSPE, the ligand is folate or N-acetyl histidine, and the drug is cabazitaxel.

* * * * *